US00PP34598P2

(12) United States Plant Patent
Diego

(10) Patent No.: US PP34,598 P2
(45) Date of Patent: Sep. 20, 2022

(54) ***RUBUS* PLANT NAMED 'BT RASFOUR'**

(50) Latin Name: *Rubus ideaus*
Varietal Denomination: BT RASFOUR

(71) Applicant: Berrytech S.R.L., Baselga di Pine (IT)

(72) Inventor: Ioriatti Diego, Baselga di Pine (IT)

(73) Assignee: Berrytech SRL

( * ) Notice: Subject to any disclaimer, the term of this patent is extended or adjusted under 35 U.S.C. 154(b) by 0 days.

(21) Appl. No.: 17/669,159

(22) Filed: Feb. 10, 2022

(51) Int. Cl.
*A01H 5/08* (2018.01)
*A01H 6/74* (2018.01)

(52) U.S. Cl.
USPC ..... Plt./204

(58) Field of Classification Search
USPC ..... Plt./156, 203, 204
See application file for complete search history.

*Primary Examiner* — Karen M Redden
(74) *Attorney, Agent, or Firm* — Cassandra Bright

(57) ABSTRACT

A new and distinct cultivar of *Rubus* plant named 'BT RASFOUR' is disclosed, characterized by very high productivity both on primocane and on floricane (production on the second year cane). Plants produce high to very high cane branching. Fruit is conical and maintains its red color during post-harvest. Plants have a high vigor. Fruit is easy to harvest, including when not at a completely ripe stage. The new variety is a *Rubus*, normally produced as an outdoor garden or container plant.

3 Drawing Sheets

Latin name of the genus and species: *Rubus ideaus.*
Variety denomination: 'BT RASFOUR'.

BACKGROUND OF THE INVENTION

The new *Rubus* cultivar is a product of a planned breeding program conducted by the inventor in Baselgia di Pine, Italy. The objective of the breeding program was to produce new *Rubus ideaus* varieties for commercial applications. The cross resulting in this new variety was made during September of 2017.

The seed parent is the, unpatented variety referred to as *Rubus* 'BP1550'. The pollen parent is the unpatented variety *Rubus* 'BPREG'. The new variety was selected during the Fall of 2018 by the inventor in a group of seedlings resulting from the 2017 crossing, in a research greenhouse in Baselgia di Pine, Italy.

Asexual reproduction of the new cultivar was performed by vegetative suckers. This was first performed at a research greenhouse in Baselgia di Pine, Italy during February of 2019 and has shown that the unique features of this cultivar are stable and reproduced true to type in multiple successive generations.

SUMMARY OF THE INVENTION

The cultivar 'BT RASFOUR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BT RASFOUR'. These characteristics in combination distinguish 'BT RASFOUR' as a new and distinct *Rubus* cultivar:

1. Very high productivity both on primocane and on floricane (production on the second year cane).
2. Branching of the cane is high to very high.

3. Fruit color is pure Red 44B even at fully ripe stage and doesn't darken.
4. High vigor.
5. Very easy fruit harvest even at not completely ripe stage.

PARENT COMPARISON

Plants of the new cultivar 'BT RASFOUR' are similar to plants of the seed parent, in most horticultural characteristics, however, plants of the new cultivar 'BT RASFOUR' differ in the following:

1. The new variety is more productive both on primocane and on floricane harvest.
2. The new variety has a more pure red colored fruit at full ripe stage, without color change.
3. The new variety has higher canes and more vigorous.
4. The new variety produces larger fruits.
5. Color of the fruit is more consistent compared to fruit of the seed parent.

Plants of the new cultivar 'BT RASFOUR' are similar to plants of the pollen parent, in most horticultural characteristics, however, plants of the new cultivar 'BT RASFOUR' differ in the following:

1. The new variety is more productive both on primocane and on floricane harvest.
2. The new variety has a more pure red colored fruit at full ripe stage.
3. The new variety has higher canes and more vigorous.
4. The new variety is less thorny on canes and leaf petioles.
5. The new variety is more resistant to warm growing conditions

COMMERCIAL COMPARISON

Plants of the new cultivar 'BT RASFOUR' are comparable to the variety *Rubus* 'BT RASTWO', U.S. Plant Pat.

No. 33,447. The two *Rubus* varieties are similar in most horticultural characteristics, however, the new variety 'BT RASFOUR' differs in the following:

1. The new variety is more productive both on primocane and on floricane harvest.
2. The new variety produces more branching canes.
3. The new variety produces higher canes and more vigorous.
4. The new variety is slightly earlier (about 5 days) in primocane fruiting
5. The new variety is less thorny on canes and leaves petiole Plants of the new cultivar 'BT RASFOUR' can also be compared to the commercial variety *Rubus* 'Amira' (unpatented). These varieties are similar in most horticultural characteristics however, the new variety 'BT RASFOUR' differs in the following:

1. The new variety is more productive both on primocane and on floricane harvest.
2. The new variety produces a more pure red, colored fruit at full ripe stage.
3. The new variety produces higher canes and more vigorous.
4. The new variety is less thorny on canes and leaf petioles.
5. The new variety is later in production (about 17 days) in primocane fruiting.

BRIEF DESCRIPTION OF THE PHOTOGRAPHS

The photographs were taken using conventional techniques and although colors may appear different from actual colors due to light reflectance it is as accurate as possible by conventional photographic techniques. Colors in the photographs may appear to differ slightly from the color values cited in the botanical description, which accurately describe the colors.

Figure 1:
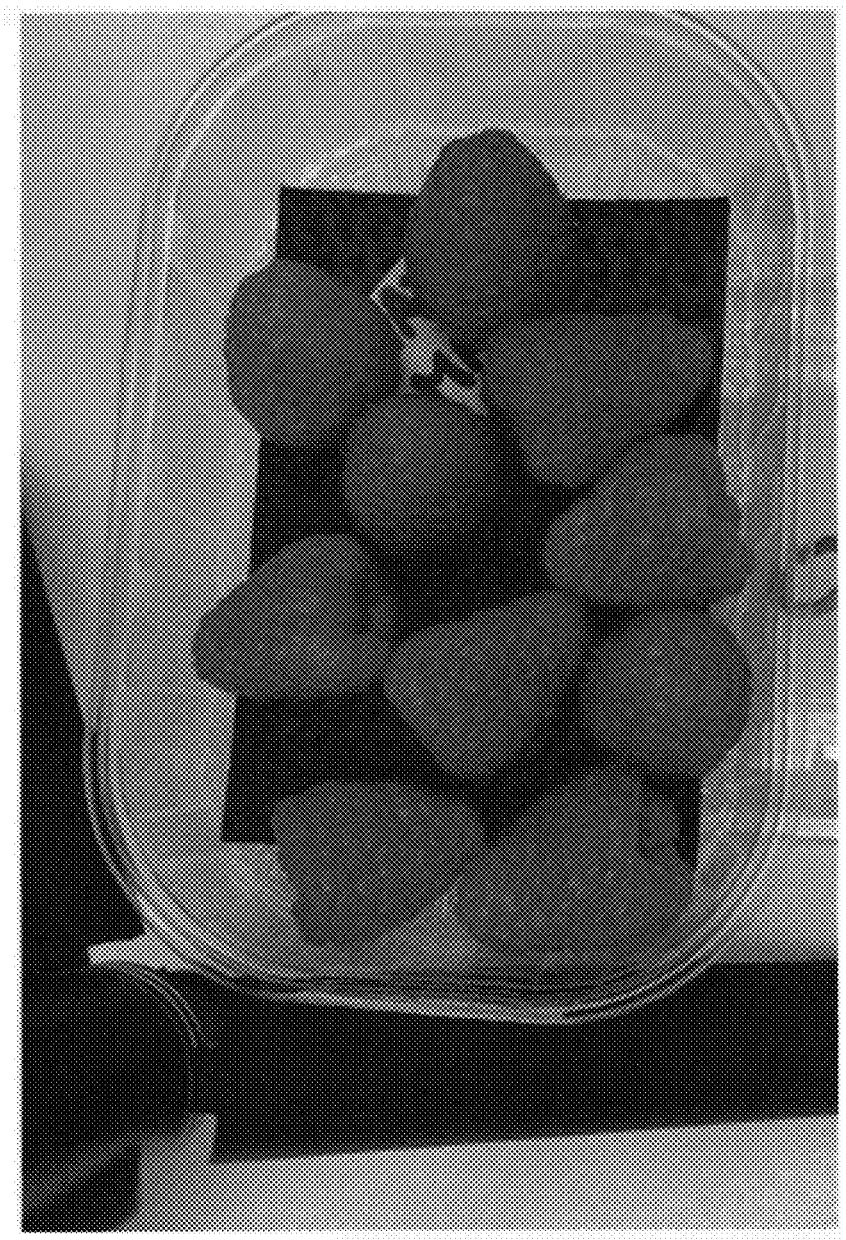
FIG. 1 illustrates in full color harvested fruit of 'BT RASFOUR'.
Figure 2:
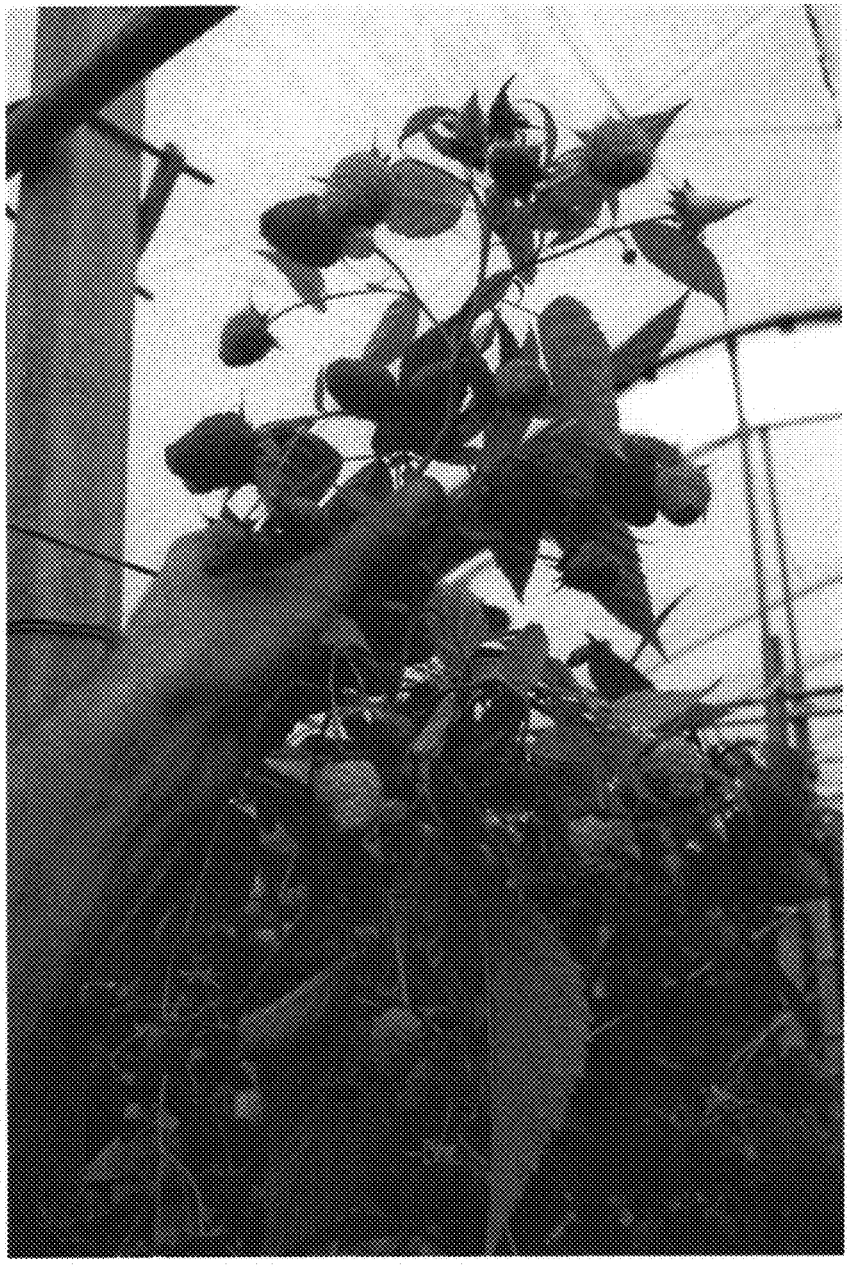
FIG. 2 illustrates in full color a typical fruiting stem of the new variety.
Figure 3:
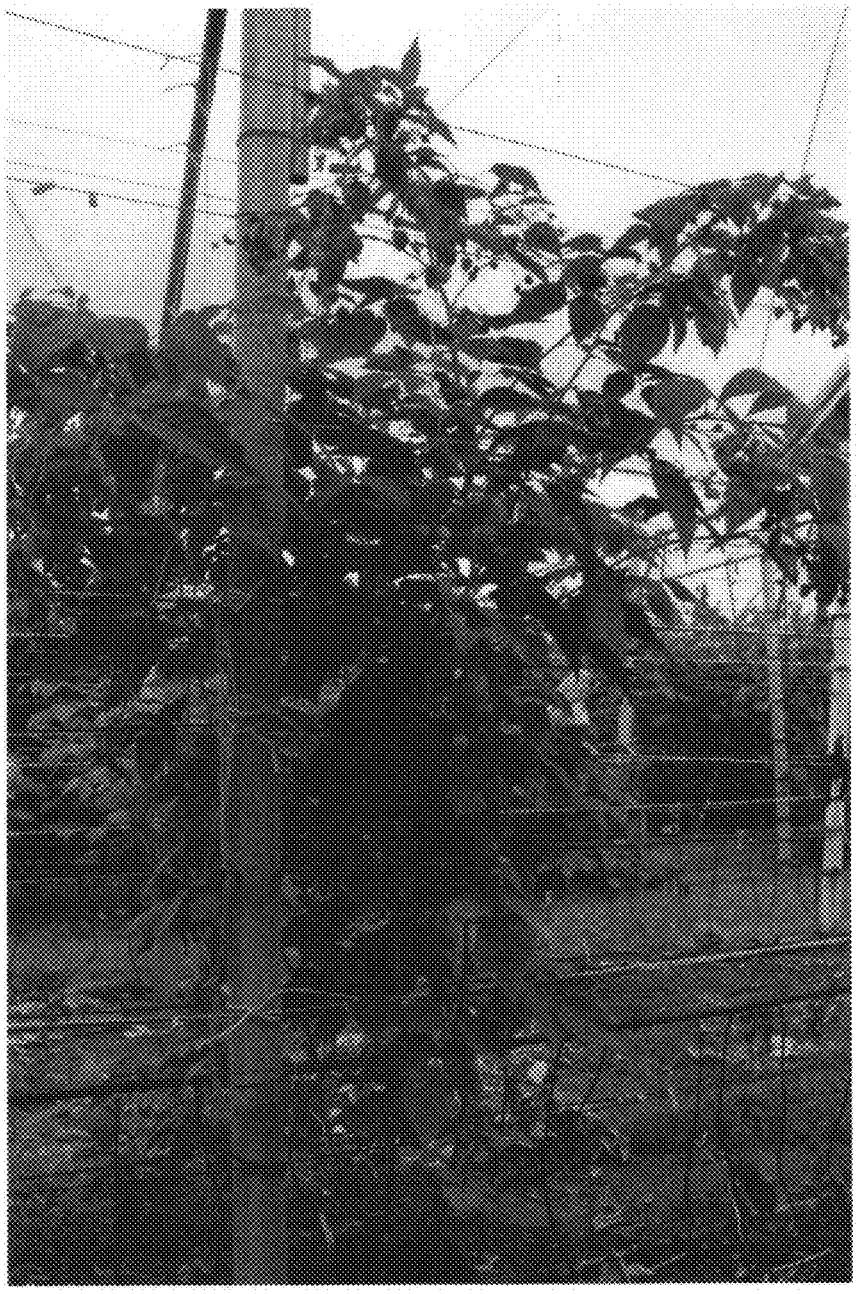
FIG. 3 illustrates in full color a typical plant of 'BT RASFOUR'.

Age of the plant is approximately 1.5 years grown in a poly hoop house.

DETAILED BOTANICAL DESCRIPTION

In the following description, color references are made to The Royal Horticultural Society Colour Chart 2007 except where general terms of ordinary dictionary significance are used. The following observations and measurements describe 'BT RASFOUR' plants which were grown in Borgo Valsugana, Trento, Italy. Plants were grown in a season tunnel, given approximately 30% shading during Summer. The growing temperature ranged from about 15° C. to 34° C. during the day and from about 8° C. to 22° C. during the night. Measurements and numerical values represent averages of typical plant types. Plants are approximately 1 year old.

Botanical classification: *Rubus ideaus* 'BT RASFOUR'.

PROPAGATION

Time to initiate roots: About 35 days at approximately 16° C.

Time to produce a rooted cutting: About 45 days at 18 ° C.

PLANT

Age of plant described: About 1 year.
Plant spread: Approximately 100 cm.
Plant height: Approximately 220 cm.
Habit: Semi-upright.
Primocane length: Approx. 220 cm.
Primocane color: Near RHS Yellow-Green N151B.
Anthocyanin coloration present: Not typical.
Dormant cane color: Near RHS Greyed-Orange 178A.
Primocane diameter: Average 1.2 cm.
Internode length: Average 6.5 cm.
Spines:
- *Approximately density/quantity of spines.*—Approximately 1 per 2 cm of stem length at 1 meter of height.
- *Length.*—Average range 2 to 3 mm.
- *Color.*—Near RHS Greyed-Purple 183C.
- *Shape.*—Short deltate.

FOLIAGE

Leaf:
- *Arrangement.*—Compound opposite.
- *Quantity.*—9-10 per stem.
- *Average length.*—Approximately 24 cm.
- *Average width.*—Approximately 22 cm.

Leaflet:
- *Quantity.*—Most common quantity of leaflets per leaf: 3.
- *Average length.*—Approximately 13-17 cm.
- *Average width.*—Approximately 8-11 cm.
- *Shape of blade.*—Overall broad deltate.
- *Apex.*—Acuminate.
- *Base.*—Broad rounded.
- *Margin.*—Double serrate.
- *Texture of top surface.*—Coriaceous.
- *Texture of bottom surface.*—Coriaceous.
- *Pubescence.*—Very little.
- *Leaf internode length.*—5-7cm.
- *Color.*—Young foliage upper side: Near RHS Yellow-Green 144B. Young foliage under side: Near RHS Green 142C. Mature foliage upper side: Near RHS Green 143A. Mature foliage under side: Near RHS Green 134B.
- *Venation.*—Type: Cross veniculate, pinnate along main axis. Venation color upper side: Near Yellow-Green 144C. Venation color under side: Near Yellow-Green 144D.
- *Petiole.*—Length: 7 cm. Width: 3 mm. Color: Near RHS Yellow-Green N144C. Texture: Glabrous.
- *Rachis.*—Length: 12-13 cm. Width: 3-4 mm. Color: Near RHS Yellow-Green N144C. Texture: Glabrous.
- *Stipules.*—Not observed.

FLOWER

Floral bud burst date: Approximately July 20 for primocane flowers.
Flowering season: Begins around August 15 in Verona, Italy.
Inflorescence:
- *Flowers per.*—18-30.

Flower size:
- *Diameter.*—Approximately 2.5 cm.
- *Length.*—Approximately 1.2 cm.

Peduncle:
*Length.*—5 cm.
*Diameter.*—0.2 cm.
*Color.*—Near RHS Yellow-Green N144C.
*Texture.*—Glabrous.

Pedicel:
*Length.*—1.3 cm.
*Diameter.*—0.2 cm.
*Color.*—Near RHS Yellow-Green N144C.
*Texture.*—Glabrous.

Petals:
*Petal arrangement.*—Rotate.
*Length.*—0.9 cm.
*Width.*—0.5 cm.
*Shape.*—Semi-cuneate.
*Margin.*—Entire.
*Apex.*—Rounded.
*Base.*—Rounded.
*Petal quantity.*—5.
*Texture.*—Glabrous.

Color:
*Petals: when opening.*—Upper surface: Near RHS White N155B. Lower surface: Near RHS White N155B.
*Fully opened.*—Upper surface: Near RHS White N155B. Lower surface: Near RHS White N155B.

Bud:
*Shape.*—Ovate.
*Length.*—Approximately 0.8 cm.
*Diameter.*—Approximately 0.4 cm.
*Color.*—Near RHS Greyed-Orange 166A.

Sepals:
*Length.*—1.5 cm.
*Width.*—0.6 cm.
*Shape.*—Narrow deltate with apiculate apex.
*Color.*—Interior Surface: Near RHS Green 140C. Exterior Surface: Near RHS Green 141B.
*Texture.*—Glabrous.

REPRODUCTIVE ORGANS

Androecium:
*Stamens.*—Number: 130. Filament length: Approximately 6 mm. Filament color: Near RHS Green-White 157A.

Anthers:
*Length.*—0.8 mm.
*Shape.*—Ovate.
*Color.*—Near RHS Greyed-Orange 164A.
*Pollen.*—Quantity: Abundant. Color: Near RHS White N155C.

Pistil:
*Number.*—130 to 140.
*Length.*—Approximately 4 mm.
*Style.*—Length: Approximately 4 mm. Color: Near RHS Green-White 157A.

FRUIT

Market use: Fresh consumption.
Length: 5.5 cm.
Diameter: 3 cm.
General shape in lateral view: Conical.
Color: Near RHS Red 44B.
Average druplets per berry: 180.
Average weight per berry: 7 grams.
Brix: 8.9.
Fruit bearing on floricane/primocane or both: Both.
Fruit begins ripening: Primocane about August 15th; floricane about April $15^{th}$.
Fruiting season: Primocane September to mid-October; floricane June to mid-July.
Yield per hectare: 22 to 28 ton/ha in primocane; 22 to 25 ton/ha in floricane.
Other fruit characteristics: Very stable pure red color also maintained after harvest. Color maintained for approximately 1 week at 4° C. Shelf life of one week at 4° C. without loss of quality.

OTHER CHARACTERISTICS

Disease/pest resistance: Observed good tolerance for raspberry aphid, *Amphorophora idaei* and leafhoppers, *Edwardsiana rosae.*
Temperature tolerance: Maximum 36° C. during pollination and harvest. Good tolerance to winter frosts to −15° C.

What is claimed is:

1. A new and distinct cultivar of *Rubus* plant named 'BT RASFOUR' as herein illustrated and described.

* * * * *